(12) United States Patent
Lerner

(10) Patent No.: US 10,729,378 B2
(45) Date of Patent: Aug. 4, 2020

(54) SYSTEMS AND METHODS OF DETECTING PROBLEMATIC HEALTH SITUATIONS

(71) Applicant: TOYOTA MOTOR NORTH AMERICA, INC., Plano, TX (US)

(72) Inventor: Emily S. Lerner, Frisco, TX (US)

(73) Assignee: TOYOTA MOTOR NORTH AMERICA, INC., Plano, TX (US)

( * ) Notice: Subject to any disclaimer, the term of this patent is extended or adjusted under 35 U.S.C. 154(b) by 0 days.

(21) Appl. No.: 16/206,345

(22) Filed: Nov. 30, 2018

(65) Prior Publication Data

US 2020/0170576 A1    Jun. 4, 2020

(51) Int. Cl.
*H04N 7/14* (2006.01)
*A61B 5/00* (2006.01)
*B60K 28/06* (2006.01)
*B60W 40/08* (2012.01)
*A61B 5/0205* (2006.01)
(Continued)

(52) U.S. Cl.
CPC .......... *A61B 5/6893* (2013.01); *A61B 5/0205* (2013.01); *B60K 28/06* (2013.01); *B60W 40/08* (2013.01); *G07C 5/008* (2013.01); *A61B 5/0002* (2013.01); *A61B 5/18* (2013.01); *B60W 2040/0818* (2013.01); *B60W 2040/0872* (2013.01); *B60W 2540/22* (2013.01)

(58) Field of Classification Search
CPC . A61B 5/69893; A61B 5/0205; A61B 5/0002; A61B 5/18; B60K 28/06; B60W 40/08; B60W 2040/0818; B60W 2040/0872; B60W 2540/22; G07C 5/008
See application file for complete search history.

(56) References Cited

U.S. PATENT DOCUMENTS

| 6,724,920 B1 | 4/2004 | Berenz et al. |
| 6,952,161 B1 | 10/2005 | Williams |
| 8,941,499 B2 | 1/2015 | Fung et al. |

(Continued)

FOREIGN PATENT DOCUMENTS

| DE | 102007048843 A1 | 6/2009 |
| DE | 102012002037 B4 | 3/2015 |

*Primary Examiner* — Munear T Akki
(74) *Attorney, Agent, or Firm* — Haynes and Boone, LLP

(57) ABSTRACT

A system for detecting a problematic health situation generally includes a vehicle. The vehicle comprises a sensor configured to detect a physiological characteristic of an occupant of the vehicle, an environmental sensor configured to detect an environmental characteristic of the vehicle, and a profile generation module including a memory. The profile generation module is configured to store a physiological characteristic measurement corresponding to the occupant of the vehicle, store an environmental characteristic measurement corresponding to the vehicle, and transmit the physiological characteristic measurement and the environmental characteristic measurement. The system comprises a server configured to compare the physiological characteristic measurement to a database of physiological characteristic measurements corresponding to the occupant of the vehicle. The server is further configured to formulate a baseline for the physiological characteristic based on the comparison of the physiological characteristic measurement and historical physiological characteristic data of the occupant of the vehicle.

20 Claims, 7 Drawing Sheets

(51) Int. Cl.
*G07C 5/00* (2006.01)
*A61B 5/18* (2006.01)

(56) References Cited

U.S. PATENT DOCUMENTS

| | | |
|---|---|---|
| 9,124,955 B2 | 9/2015 | Geva et al. |
| 9,883,369 B2 | 1/2018 | Ulmansky et al. |
| 9,988,055 B1 | 6/2018 | O'Flaherty et al. |
| 10,007,263 B1 | 6/2018 | Fields et al. |
| 2007/0257804 A1* | 11/2007 | Gunderson .......... G07C 5/0891 340/576 |
| 2013/0070043 A1* | 3/2013 | Geva ................... B60K 28/066 348/14.02 |
| 2015/0379362 A1 | 12/2015 | Calmes et al. |

* cited by examiner

SYSTEMS AND METHODS OF DETECTING PROBLEMATIC HEALTH SITUATIONS

TECHNICAL FIELD

The present disclosure relates generally to problematic situation identification and, more particularly, to identifying problematic health situations utilizing vehicle sensors.

BACKGROUND

The ability of vehicles to identify medical emergency situations and properly address those situations is limited. A more predictable and reliable method is needed to detect emergency situations for occupants of a vehicle, particularly the driver. The ability of a vehicle to detect an emergency situation and properly respond to that situation may allow for quicker access to medical assistance when such assistance is needed. Further, a detection system that is reliable and reduces the amount of false reports may more properly and efficiently address medical emergencies. Existing systems lack the ability to reliably detect whether the occupant of a vehicle is experiencing a medical emergency. This can lead to the improper allocation of emergency assistance resources, which can result in increased injury to vehicle occupants who are actually experiencing potentially life-threatening situations. It would therefore be desirable to enable a vehicle to accurately, repeatably, and reliably detect when an occupant in the vehicle is experiencing a medical emergency. Therefore, what is needed is an apparatus, system, and/or method that addresses one or more of the foregoing issues, and/or one or more other issues.

SUMMARY

The present disclosure provides systems and methods for monitoring vehicle occupants, determining when one or more of the vehicle occupants is experiencing a problematic health situation, and responding appropriately to address the situation. A generalized system for detecting a problematic health situation includes a vehicle. The vehicle includes a sensor configured to detect a physiological characteristic of an occupant of the vehicle. The vehicle further includes an environmental sensor configured to detect an environmental characteristic of the vehicle. The vehicle further includes a profile generation module including a memory. The profile generation module is configured to store a physiological characteristic measurement corresponding to the occupant of the vehicle in the memory. The profile generation module is further configured to store an environmental characteristic measurement corresponding to the vehicle in the memory. The profile generation module is further configured to transmit the physiological characteristic measurement and the environmental characteristic measurement. The system further includes a server configured to compare the physiological characteristic measurement to a database of physiological characteristic measurements corresponding to the occupant of the vehicle. The database includes historical physiological characteristic data of the occupant of the vehicle. The server is further configured to formulate a baseline for the physiological characteristic of the occupant of the vehicle based on the comparison of the physiological characteristic measurement and the historical physiological characteristic data of the occupant of the vehicle.

An additional generalized system for detecting a problematic health situation includes a vehicle. The vehicle includes a sensor configured to detect a physiological characteristic of an occupant of the vehicle. The vehicle further includes an environmental sensor configured to detect an environmental characteristic of the vehicle. The vehicle further includes a profile generation module including a memory. The system further includes a server configured to compare a physiological characteristic measurement corresponding to the occupant of the vehicle to a database of physiological characteristic measurements corresponding to the occupant of the vehicle. The database includes historical physiological characteristic data of the occupant of the vehicle. The server is further configured to formulate a baseline for the physiological characteristic of the occupant of the vehicle based on the comparison of the physiological characteristic measurement corresponding to the occupant of the vehicle and the historical physiological characteristic data of the occupant of the vehicle. The server is further configured to determine whether the physiological characteristic measurement is outside the baseline, determine whether an environmental characteristic measurement is abnormal, and determine whether the occupant of the vehicle is experiencing a problematic health situation.

A generalized method for detecting a problematic health situation includes detecting a physiological characteristic of an occupant of a vehicle. The method further includes detecting an environmental characteristic of the vehicle. The method further includes transmitting, by a profile generation module of the vehicle, a physiological characteristic measurement corresponding to the occupant of the vehicle and an environmental characteristic measurement corresponding to the vehicle. The method further includes comparing the physiological characteristic measurement to a database of physiological characteristic measurements of the occupant of the vehicle. The database includes historical physiological characteristic data of the occupant of the vehicle. The method further includes formulating a baseline for the physiological characteristic of the occupant of the vehicle based on the comparison of the physiological characteristic measurement and the historical physiological characteristic data of the occupant of the vehicle.

An additional generalized system for detecting a problematic health situation includes a first vehicle in a geographic area. The first vehicle is configured to detect a physiological characteristic of an occupant of the first vehicle and an environmental characteristic of the first vehicle. The system further includes a second vehicle in the geographic area. The second vehicle is configured to detect a physiological characteristic of an occupant of the second vehicle and an environmental characteristic of the second vehicle. The system further includes a sever configured to compare a physiological characteristic measurement corresponding to the occupant of the first vehicle to a physiological characteristic measurement corresponding to the occupant of the second vehicle. The server is further configured to determine, based on the comparison, that the occupant of the first vehicle is experiencing a problematic health situation. The server is further configured to determine a response.

DETAILED DESCRIPTION

Figure 1:
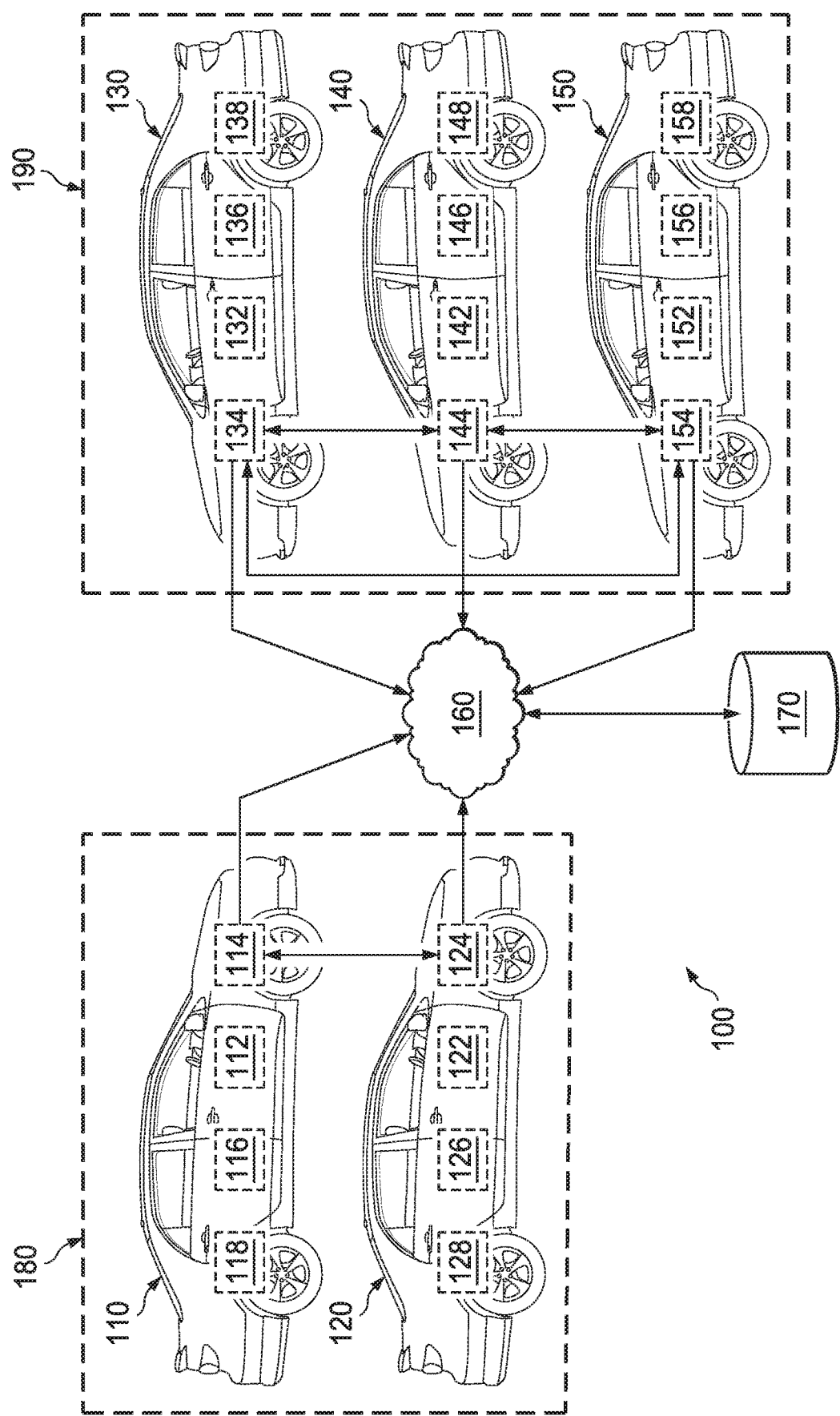
FIG. 1 is a diagrammatic illustration of a system for detecting an emergency situation according to one or more embodiments of the present disclosure.

For the purposes of promoting an understanding of the principles of the invention, reference will now be made to certain implementations, or examples, illustrated in the drawings, and specific language will be used to describe the same. It will nevertheless be understood that no limitation of the scope of the invention is thereby intended. Any alterations and further modifications in the described implementations, and any further applications of the principles of the invention as described herein are contemplated as would normally occur to one skilled in the art to which the invention relates.

This disclosure describes a system for detecting when vehicle occupants experience problematic health situations (which may be an emergency situation) and responding to those situations. In the system, sensors in a vehicle monitor, record, and/or detect physiological characteristics of an occupant of the vehicle. Additionally, environmental sensors monitor, record, and/or detect environmental characteristics of the vehicle itself. By detecting the physiological characteristics of the vehicle occupant, receiving physiological characteristic measurements, and using machine learning, the system can determine a baseline for each physiological characteristic corresponding to a specific vehicle occupant (e.g., a driver of the vehicle). The system can then compare newly received physiological characteristic measurements with the baseline for that particular physiological characteristic to determine whether the newly received physiological characteristic measurement is outside the baseline. When the physiological characteristic measurement is outside of the baseline, the system then determines if the physiological characteristic measurement is similar to a physiological characteristic measurement of an occupant of a second vehicle. If the compared physiological characteristic measurements are not similar, then the system determines whether the environmental conditions of the vehicle are normal or abnormal by analyzing a received environmental characteristic measurement. If the environmental conditions are abnormal, then the system determines that the vehicle occupant is experiencing an problematic health situation and initiates an appropriate response.

FIG. 1 is a diagrammatic illustration of a system for detecting a problematic health situation (which may be an emergency situation) according to one or more embodiments of the present disclosure. In at least one such embodiment, as illustrated in FIG. 1, the system is generally referred to by the reference numeral 100 and includes a vehicle 110, a vehicle 120, a cloud server 160, a profile database 170, and a geographic area 180. In several examples, the profile database 170 includes one or more occupant profiles and one or more vehicle profiles, which will be discussed in further detail below. The detection system 100 optionally includes additional vehicles, such as vehicle 130, vehicle 140, and vehicle 150, as shown in FIG. 1. The optional vehicles 130, 140, 150 are located within a geographic area 190, as further shown in FIG. 1, which is different than the geographic area 180. Additionally, the detection system 100 optionally includes additional profile databases. In the embodiment of FIG. 1, each of the vehicles 110, 120, 130, 140, 150 are automobiles. While in FIG. 1 the vehicles 110, 120, 130, 140, 150 are depicted as cars, it is to be understood that the vehicles 110, 120, 130, 140, 150 may be any other type of suitable automobile (e.g., a pickup truck, a semi truck, a fleet vehicle, etc.). The vehicle 110 includes a human-machine interface (HMI) 112 (which may be a user interface), a profile generation module 114, a sensor 116, and an environmental sensor 118. The HMI 112 is operably coupled to, and adapted to be in communication with, the profile generation module 114. The sensor 116 is also operably coupled to, and adapted to be in communication with, the profile generation module 114. Further, the environmental sensor 118 is operably coupled to, and adapted to be in communication with, the profile generation module 114. The profile generation module 114 is operably coupled to, and adapted to be in communication with, the cloud server 160. Additionally, the vehicle 110 is operably coupled to, and adapted to be in communication with the profile database 170, which is itself operably coupled to, and adapted to be in communication with, the cloud server 160.

Like the vehicle 110, the vehicle 120 includes a human-machine interface (HMI) 122, a profile generation module 124, a sensor 126, and an environmental sensor 128. The HMI 122 is operably coupled to, and adapted to be in communication with, the profile generation module 124. The sensor 126 is also operably coupled to, and adapted to be in communication with, the profile generation module 124. Further, the environmental sensor 128 is operably coupled to, and adapted to be in communication with, the profile generation module 124. The profile generation module 124 is operably coupled to, and adapted to be in communication with, the cloud server 160.

The vehicle 130 includes a human-machine interface (HMI) 132, a profile generation module 134, a sensor 136, and an environmental sensor 138. The HMI 132 is operably coupled to, and adapted to be in communication with, the profile generation module 134. The sensor 136 is also operably coupled to, and adapted to be in communication with, the profile generation module 134. Further, the environmental sensor 138 is operably coupled to, and adapted to be in communication with, the profile generation module 134. The profile generation module 134 is operably coupled to, and adapted to be in communication with, the cloud server 160.

The vehicle 140 includes a human-machine interface (HMI) 142, a profile generation module 144, a sensor 146, and an environmental sensor 148. The HMI 142 is operably coupled to, and adapted to be in communication with, the profile generation module 144. The sensor 146 is also operably coupled to, and adapted to be in communication with, the profile generation module 144. Further, the environmental sensor 148 is operably coupled to, and adapted to be in communication with, the profile generation module 144. The profile generation module 144 is operably coupled to, and adapted to be in communication with, the cloud server 160.

The vehicle 150 includes a human-machine interface (HMI) 152, a profile generation module 154, a sensor 156, and an environmental sensor 158. The HMI 152 is operably coupled to, and adapted to be in communication with, the profile generation module 154. The sensor 156 is also operably coupled to, and adapted to be in communication with, the profile generation module 154. Further, the environmental sensor 158 is operably coupled to, and adapted to be in communication with, the profile generation module 154. The profile generation module 154 is operably coupled to, and adapted to be in communication with, the cloud server 160.

As shown in FIG. 1, each profile generation module within a defined geographic area is adapted to be in communication with one or more of each of the other profile generation modules in the defined geographic area via vehicle-to-vehicle (V2V) communication. For example, in the geographic area 180, the profile generation module 114 can transmit signals to and receive signals from the profile generation module 124, as will be described in further detail below. As another example, in the geographic area 190, the profile generation modules 134, 144, 154 can transmit signals to and receive signals from each of the other profile generation modules 144, 154, 134. Additionally, while FIG. 1 only illustrates the profile generation module 114 in communication with the cloud server 160, it is to be understood that the profile generation module 114 may also communicate with the profile database 170. In several embodiments, the geographic area 180 may be defined as an area within one mile of the vehicle 110, or an area any other suitable distance from the vehicle 110, which may be less than or greater than one mile from the vehicle 110.

Figure 2:
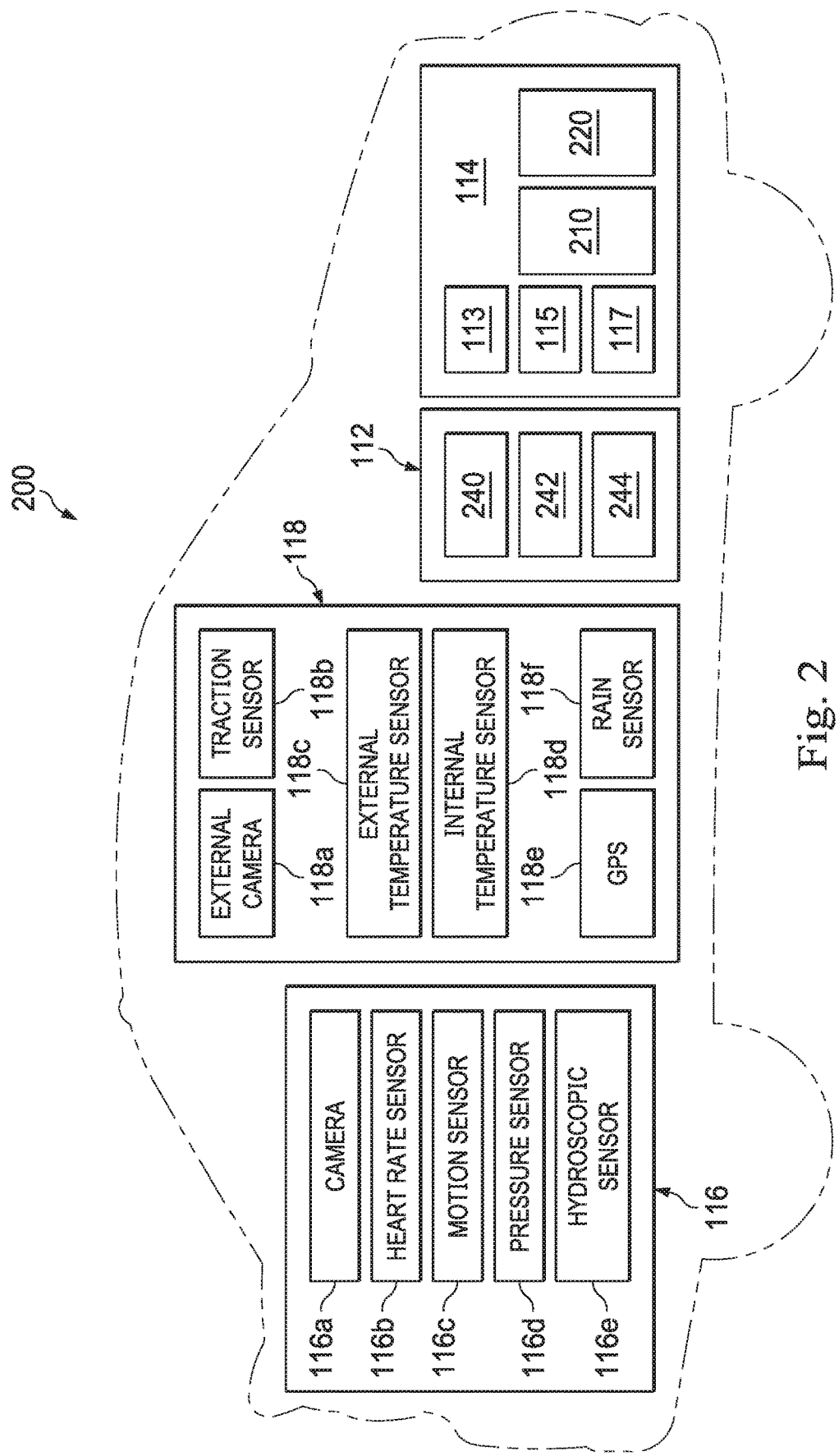
FIG. 2 is a diagrammatic illustration of an apparatus according to one or more embodiments of the present disclosure.

FIG. 2 is a diagrammatic illustration of an apparatus according to one or more embodiments of the present disclosure. In at least one such embodiment, as illustrated in FIG. 2, the apparatus is generally referred to by the reference numeral 200 and may represent any one of the vehicles in FIG. 1. As can be seen in FIG. 2, the apparatus 200 includes the components of the vehicle 110, which components are given the same reference numerals. In the embodiment shown in FIG. 2, the profile generation module 114 includes a receiver 113, a sensor processing module 115, a transmitter 117, an occupant profile 210, and a vehicle profile 220. In several embodiments, the transmitter 117 and the receiver 113 are combined into a transceiver capable of both sending and receiving wireless signals. The receiver 113 is operably coupled to, and adapted to be in communication with, one or more of the sensor 116, the environmental sensor 118, the sensor processing module 115, the transmitter 117, and the HMI 112.

The HMI 112, which is operably coupled to, and adapted to be in communication with, the profile generation module 114, includes a display unit 240, an input/output (I/O) device 242, and a communication device 244, which may be a Bluetooth or other wireless or wired device. The I/O device 242 may be in the form of a communication port (e.g., a USB port), a touch-screen display unit, soft keys associated with a dashboard, a steering wheel, and/or other similar components of the vehicle 110. The display unit 240 may be, include, or be part of a plurality of display units arranged to show a visual output to a user. For example, in several embodiments, the display unit 240 may include one, or any combination, of a central display unit associated with the dashboard of the vehicle 110, an instrument cluster display unit associated with an instrument cluster of the vehicle 110, and a heads-up display unit associated with the dashboard and a windshield of the vehicle 110. Thus, as used herein the reference numeral 240 may refer to one, or a combination, of said display units.

The sensor 116, which is operably coupled to, and adapted to be in communication with, the profile generation module 114, may be, include, or be part of one or more sensors positioned in the interior of the vehicle 110, for example. In several embodiments, the sensor 116 may include one, or any combination, of a camera 116a, a heart rate sensor 116b, a motion sensor 116c, a pressure sensor 116d, a hydroscopic sensor 116e, and any other suitable sensor. Thus, as used herein the reference numeral 116 may refer to one, or a combination, of the above sensors. In several embodiments, the sensor 116 includes any other sensor capable of identifying and/or communicating with another vehicle (e.g., an RFID sensor, a Bluetooth sensor, etc.).

In several examples, the camera 116a captures images and/or video of the vehicle occupant's face and/or body as the vehicle 110 moves along the road. The captured images are used to determine whether the vehicle occupant (which may be the driver or a passenger of the vehicle 110) is experiencing a high stress and/or emergency situation, which will be described in further detail below. In some embodiments, the camera 116a may be mounted on any one or more of a rearview mirror, a dashboard, a steering wheel, a windshield, or on any other suitable component. In some embodiments, multiple cameras 116a may be positioned within the interior of the vehicle 110 to capture several angles of the face of the vehicle occupant. Capturing multiple camera angles allows the sensor processing module 115 to generate a three-dimensional rendering of the vehicle occupant's face. This three-dimensional rendering may be used to determine a baseline measurement for a physiological characteristic of the vehicle occupant, which will be discussed in further detail below.

In several embodiments, the heart rate sensor 116b measures the heart rate of the vehicle occupant (e.g., the driver of the vehicle 110). The captured heart rate data is used to determine whether the vehicle occupant is experiencing a high stress and/or emergency situation, which will be described in further detail below. In several examples, the heart rate sensor 116b is positioned on and/or within a seatbelt of the vehicle 110, such as the seatbelt worn by the vehicle occupant, which may be the driver of the vehicle 110 or a passenger of the vehicle 110. As an example, the heart rate sensor 116b may be positioned on and/or within a portion of the seatbelt that covers the vehicle occupant's heart. In other examples, to ensure that the heart rate sensor 116b accurately measures the heartrate of the vehicle occupant, several heartrate sensors may be placed on and/or within the seatbelt. This helps to guarantee that at least one heart rate sensor 116b is located near the vehicle occupant's heart, regardless of any difference in body size of the vehicle occupant (e.g., a difference in body size between an adult and a child).

In some embodiments, the motion sensor 116c measures the breathing rate of the vehicle occupant (e.g., the driver or a passenger of the vehicle 110). The captured breathing rate data is used to determine whether the vehicle occupant is experiencing a high stress and/or emergency situation, which will be described in further detail below. In several examples, the motion sensor 116c is positioned on and/or within the vehicle occupant's seatbelt in the vehicle 110. The motion sensor 116c may be positioned within a portion of the seatbelt that lays across the vehicle occupant's lap, stomach, and/or chest. In some embodiments, the motion sensor 116c detects the vehicle occupant's breathing pattern by detecting expansion and contraction of the seatbelt as the vehicle occupant breathes.

In some embodiments, the pressure sensor 116d measures the grip pressure of the vehicle occupant (e.g., the driver of the vehicle 110) as the vehicle occupant grips a steering wheel of the vehicle 110. The captured pressure data is used to determine whether the vehicle occupant is experiencing a high stress and/or emergency situation, which will be described in further detail below. In several examples, the pressure sensor 116d is positioned on and/or within the steering wheel of the vehicle 110. In some examples, the pressure sensor 116d is positioned on and/or within one or more portions of the steering wheel, such as the portions corresponding to the "10:00" and "2:00" positions of the steering wheel. In other examples, several pressure sensors 116d are positioned around the entire circumference of the steering wheel. This helps ensure that the pressure sensor 116d accurately measures the grip pressure of the vehicle occupant regardless of where the vehicle occupant's hands are located on the steering wheel.

In some embodiments, the hydroscopic sensor 116e measures whether moisture is discharged from the hands and/or arms, for example, of the vehicle occupant (e.g., the driver of the vehicle 110) as the vehicle occupant grips and/or contacts the steering wheel of the vehicle 110. The captured data is used to determine whether the vehicle occupant is experiencing a high stress and/or emergency situation, which will be described in further detail below. In several examples, the hydroscopic sensor 116e is also positioned on and/or within the steering wheel of the vehicle 110. Like the pressure sensor 116d, the hydroscopic sensor 116e is positioned within one or more portions of the steering wheel, such as the portions corresponding to the "10:00" and "2:00" positions of the steering wheel. In other examples, several hydroscopic sensors 116e are positioned around the entire circumference of the steering wheel. This helps ensure that the hydroscopic sensor 116e accurately detects any moisture (e.g., sweat) discharged from the vehicle occupant's hands and/or arms regardless of where the vehicle occupant's hands are located on the steering wheel.

In several embodiments, the sensor 116 is adapted to transmit data (e.g., physiological characteristic measurements) to the receiver 113 of the profile generation module 114. In several embodiments, the sensor 116 transmits data to the receiver 113 in set, recurring time intervals. For example, the sensor 116 may transmit data to the receiver 113 at a transmission frequency rate that may range from about one time per second to one time per minute. In some examples, the transmission frequency may be about one time every five seconds, one time every thirty seconds, or any other suitable interval of time. The transmission frequency provided herein is for example only, and other embodiments may include more frequent transmissions or less frequent transmissions. For example, in some implementations, the transmission frequency may be faster than one time per second or slower than one time per minute. In some embodiments, for example, the data transmitted from the camera 116a to the receiver 113 includes images captured by each of the one or more cameras of the camera 116a. In such examples, the sensor 116 can capture images of the vehicle occupant's face and/or the vehicle occupant's body as the vehicle 110 travels along a road.

In some embodiments, the data transmitted by the sensor 116 is received by the sensor processing module 115. The data may be received by the sensor processing module 115 directly from the sensor 116, or the data may be received by the sensor processing module 115 indirectly from the sensor 116 via the receiver 113. In some examples, the sensor processing module 115 includes an image processor and/or an image processing module. In several embodiments, the sensor processing module 115 is adapted to read the data received from the sensor 116, analyze the data, process the data, and output the processed data to the transmitter 117. In several embodiments, the transmitter 117 then transmits the data to the cloud server 160, which will be described in further detail below. In alternative embodiments, the transmitter 117 transmits the data directly to the profile database 170.

The environmental sensor 118, which is operably coupled to, and adapted to be in communication with, the profile generation module 114, may be, include, or be part of one or more sensors positioned in the interior and/or the exterior of the vehicle 110, for example. In several embodiments, the environmental sensor 118 may include one, or any combination, of a camera 118a (which may be one or more external cameras mounted on the vehicle 110), a traction sensor 118b, an external temperature sensor 118c, an internal temperature sensor 118d, a GPS receiver 118e, a rain sensor 118f, and any other suitable sensor. Thus, as used herein the reference numeral 118 may refer to one, or a combination, of the above sensors.

In several embodiments, the camera 118a may include one, or any combination, of a front camera associated with a front portion of the vehicle 110, a rear camera associated with a rear portion of the vehicle 110, a side camera associated with a right side portion of the vehicle 110, a side camera associated with a left side portion of the vehicle 110, and any other camera located on the vehicle 110. Thus, as used herein the reference numeral 118a may refer to one, or a combination, of the exterior vehicle cameras. In several examples, the camera 118a captures images of the exterior environment surrounding the vehicle 110 as the vehicle 110 travels along a road.

In several examples, the traction sensor 118b measures how well the tires of the vehicle 110 grip the surface of the road on which the vehicle 110 is traveling. The captured traction data is used to determine whether the vehicle 110 is slipping and/or sliding on the road. This data may be used to determine whether the environmental conditions of the vehicle 110 are normal or abnormal, which will be discussed in further detail below. In several examples, the external temperature sensor 118c measures the temperature of the air surrounding the vehicle 110. This temperature data may be used to determine whether the environmental conditions of the vehicle 110 are normal or abnormal, which will be discussed in further detail below. In several examples, the internal temperature sensor 118d measures the temperature of the air in the interior of the vehicle 110. This temperature data may be used to determine whether the environmental conditions of the vehicle 110 are normal or abnormal, which will be discussed in further detail below.

The GPS receiver 118e is adapted to record location data of the vehicle 110. In some embodiments, the location data may be used to determine the weather conditions for the geographic area where the vehicle 110 is located. This location data may be used to determine whether the environmental conditions of the vehicle 110 are normal or abnormal, which will be discussed in further detail below. In several examples, the rain sensor 118f measures whether rain is falling on a windshield of the vehicle 110 and, if so, how much rain is falling. In other examples, the rain sensor 118f measures whether rain is falling on a rear window, one or more side windows, or any other portion of the vehicle 110. The captured rain data is used to determine whether the vehicle 110 is driving through rain. This data may be used to determine whether the environmental conditions of the vehicle 110 are normal or abnormal, which will be discussed in further detail below.

While the above discussion with respect to FIG. 2 has been made with reference to the vehicle 110, it is to be understood that the above discussion also applies to each of the vehicles 120, 130, 140, 150 and their corresponding components.

Figure 3:
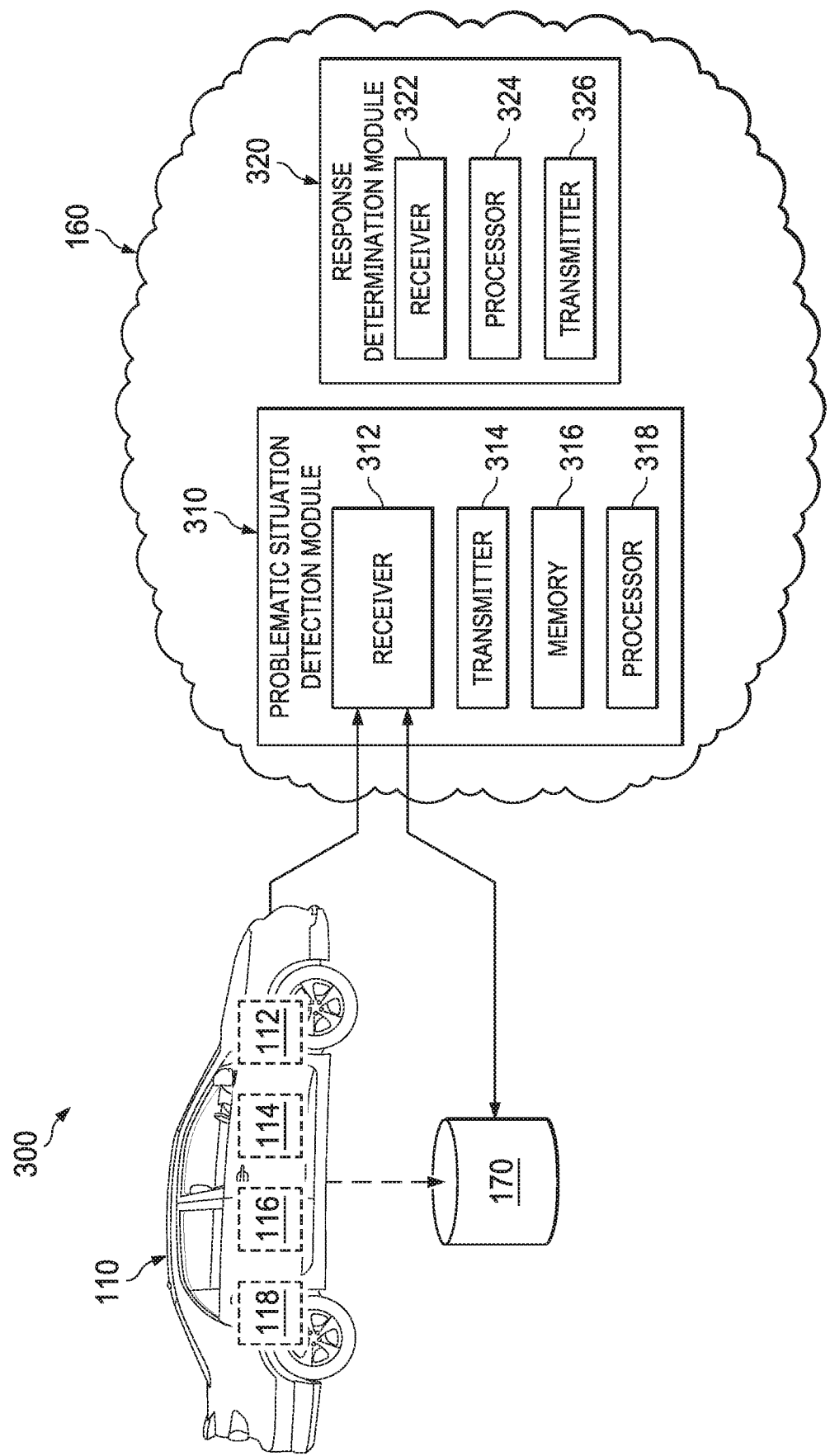
FIG. 3 is a diagrammatic illustration of a system in operation according to one or more embodiments of the present disclosure.

FIG. 3 is a diagrammatic illustration of a system in operation according to one or more embodiments of the present disclosure. In at least one such embodiment, as illustrated in FIG. 3, the system is generally referred to by the reference numeral 300 and includes the components of the detection system 100, which components are given the same reference numerals. In the embodiment shown in FIG. 3, in addition to the system having certain components of the detection system 100, the cloud server 160 of the system 300 includes a problematic situation detection module 310 and a response determination module 320. In the embodiment shown in FIG. 3, the problematic situation detection module 310 includes a receiver 312, a transmitter 314, a memory 316, and a processor 318. In several embodiments, the transmitter 314 and the receiver 312 are combined into a transceiver capable of both sending and receiving wireless or wired signals. The receiver 312 is operably coupled to, and adapted to be in communication with, one or more of the HMI 112 (see FIG. 2), the sensor processing module 115 (see FIG. 2), the transmitter 314, and the profile database 170. In the embodiment shown in FIG. 3, the response determination module 320 includes a receiver 322, a processor 324, and a transmitter 326. In several embodiments, the transmitter 326 and the receiver 322 are combined into a transceiver capable of both sending and receiving wireless or wired signals. The receiver 322 is operably coupled to, and adapted to be in communication with, one or more of the HMI 112, the transmitter 117, and the transmitter 314 of the problematic situation detection module 310.

In several embodiments, the memory 316 is operably coupled to, and adapted to be in communication with, the receiver 312. In several embodiments, the receiver 312 is adapted to receive one or more data transmissions (which may be physiological characteristic measurements and environmental characteristic measurements) from the transmitter 117 of the profile generation module 114 carried on the vehicle 110. In several other embodiments, the receiver 312 is adapted to receive, in addition to or in lieu of the data transmissions received from the transmitter 117, data transmissions from the profile database 170, which will be discussed in further detail below. The receiver 312 is adapted to output each of the one or more data transmissions to the memory 316, and the memory 316 stores each of the one or more data transmissions for a set period of time before discarding the data transmissions. In several embodiments, the data transmissions are stored in a historical record. In some examples, the set period of time for which the memory 316 stores the data transmission(s) includes one minute, two minutes, five minutes, ten minutes, or any other suitable period of time, which may be less than one minute or more than ten minutes. Therefore, the memory 316, in some embodiments, maintains the historical record of all the data transmissions received by the receiver 312 from the transmitter 117. In several alternative embodiments, the historical record includes historical physiological characteristic data of the occupant of the vehicle 110.

In several alternative embodiments, the receiver 312 is adapted to output each of the one or more data transmissions to the profile database 170, and the profile database 170 stores each of the one or more data transmissions for a set period of time before discarding the data transmissions. In several embodiments, the data transmissions are stored in a historical record. In some examples, the set period of time for which the profile database 170 stores the data transmission(s) includes one minute, two minutes, five minutes, ten minutes, or any other suitable period of time, which may be less than one minute or more than ten minutes. Therefore, the profile database 170, in some embodiments, maintains the historical record of all the data transmissions received by the receiver 312 from the transmitter 314. In several alternative embodiments, the historical record includes historical physiological characteristic data of the occupant of the vehicle 110.

In several embodiments, the processor 318 is further adapted to determine whether one or more physiological characteristic measurements corresponding to the vehicle occupant are outside of the baseline for each particular physiological characteristic, which will be discussed in further detail below. In some examples, the processor 318 is adapted to determine if one or more physiological characteristic measurements corresponding to the vehicle occupant are similar to physiological characteristic measurements corresponding to occupants of one or more other vehicles (e.g., the vehicle 120), which will be discussed in further detail below. Additionally, the processor 318 is adapted to determine whether the environmental conditions of the vehicle 110 are normal or abnormal, which will be discussed in further detail below. In several examples, after such determinations are made, the transmitter 314 of the problematic situation detection module 310 transmits a signal to the response determination module 320, which may then transmit the signal to the profile generation module 114 of the vehicle 110, for example. In several embodiments, the signal includes response instructions (e.g., instructions ordering the vehicle 110 to enter autonomous mode), which will be discussed in further detail below.

In several embodiments, the processor 324 of the response determination module 320 is operably coupled to, and adapted to be in communication with, the receiver 322 and the transmitter 326. In some embodiments, the processor 324 is adapted to read and analyze one or more data transmissions received from the receiver 322. In several embodiments, the response determination module 320 is adapted to determine an appropriate response based on the one or more data transmissions received from the receiver 322. In some examples, the transmitter 326 transmits the determined emergency response to the profile generation module 114 of the vehicle 110. Then, in such embodiments, the profile generation module 114 initiates the emergency response. For example, if the driver of the vehicle 110 is experiencing a heart attack, the profile generation module 114 may command the vehicle 110 to automatically stop moving, activate the hazard signals, and transmit a GPS signal to the server 160. In several embodiments, the server 160 is connected to and transmits the heart attack information to hospitals, ambulances, fire trucks, and other similar emergency responders. In further examples, when an emergency situation is detected while the vehicle 110 is operating in a non-autonomous driving mode, the profile generation module 114 may automatically initiate an autonomous driving mode of the vehicle 110, if available. In several additional examples, the vehicle 110 may communicate with other vehicles in the same geographic area (e.g., the geographic area 180) as the vehicle 110 using vehicle-to-vehicle (V2V) communication. In such examples, the vehicle 110 may use V2V communication to generate the best and/or fastest route to a hospital or other appropriate medical care facility.

Figure 4A:
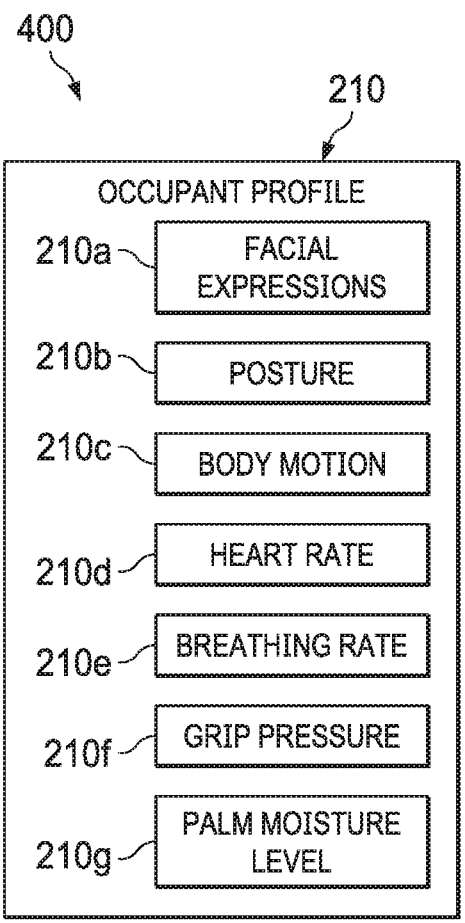
FIG. 4A is a diagrammatic illustration of an occupant profile according to one or more embodiments of the present disclosure.

FIG. 4A is a diagrammatic illustration of an apparatus according to one or more embodiments of the present disclosure. In at least one such embodiment, as illustrated in FIG. 4A, the apparatus is generally referred to by the reference numeral 400 and includes the components of the apparatus 200 and the system 300, which components are given the same reference numerals. In the embodiment shown in FIG. 4A, in addition to the apparatus 400 having certain components of the apparatus 200 and the system 300, the occupant profile 210 of the apparatus 400 includes several physiological characteristics of the occupant of the vehicle 110 (e.g., the driver or a passenger). The physiological characteristics in the occupant profile 210 are each adapted to be measured, tracked, and/or monitored by one or more of the sensors 116, as described above. In some examples, the physiological characteristics of the occupant in the occupant profile 210 include one or more facial expressions 210*a*, a posture 210*b*, body motion 210*c*, a heart rate 210*d*, a breathing rate 210*e*, a grip pressure 210*f*, and a palm moisture level 210*g*.

As discussed above and as will be discussed in further detail below, the processor 318 of the problematic situation detection module 310 is adapted to analyze the physiological characteristics and any physiological characteristic measurements to determine a baseline (which may be a range of values) for each physiological characteristic. Each occupant of the vehicle 110 has an occupant profile (e.g., the occupant profile 210) specific to that occupant. For example, the driver of the vehicle 110 has an occupant profile that may be, and likely will be, different from the occupant profile for a passenger of the vehicle 110. In several embodiments, the occupant profile 210 corresponds to the driver of the vehicle 110. In some embodiments, the baseline for each physiological characteristic includes a range of values. Because each occupant of the vehicle 110 has a different occupant profile, each occupant profile may, and likely will, include different baselines for each physiological characteristic when compared with the same physiological characteristic of another occupant profile. For example, the baseline for the heart rate 210*d* of the driver of the vehicle 110 may include a range of 60 beats per minute (BPM) to 65 BPM. In contrast, the baseline for the heart rate 210*d* of a passenger of the vehicle 110 may include a range of 50 BPM to 55 BPM. In several embodiments, the processor 318 is adapted to transmit the determined baselines to the memory 316 for storage. In several other examples, the processor 318 transmits the determined baselines to a baseline archive, which will be discussed in further detail below. As will be discussed in further detail below, the processor 318 is adapted to determine the baselines for each physiological characteristic using machine learning.

Figure 4B:
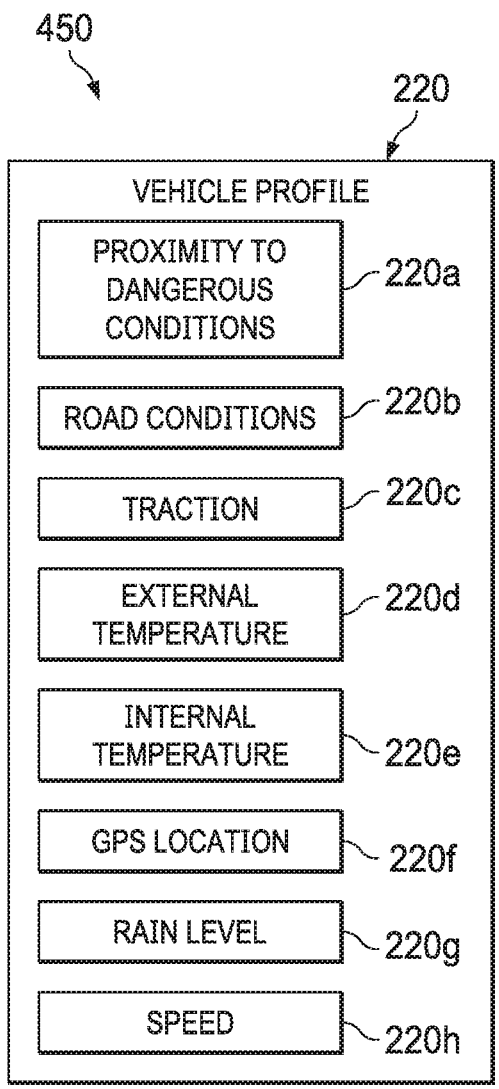
FIG. 4B is a diagrammatic illustration of a vehicle profile according to one or more embodiments of the present disclosure.

FIG. 4B is a diagrammatic illustration of an apparatus according to one or more embodiments of the present disclosure. In at least one such embodiment, as illustrated in FIG. 4B, the apparatus is generally referred to by the reference numeral 450 and includes the components of the apparatus 200 and the system 300, which components are given the same reference numerals. In the embodiment shown in FIG. 4B, in addition to the apparatus 450 having certain components of the apparatus 200 and the system 300, the vehicle profile 220 of the apparatus 450 includes several environmental characteristics of the vehicle 110. The environmental characteristics in the vehicle profile 220 are each adapted to be measured, tracked, and/or monitored by one or more of the environmental sensors 118, as described above. In some examples, the environmental characteristics of the vehicle 110 in the vehicle profile 220 include a proximity to dangerous conditions 220*a* (which may be detected by the external camera 118*a*), road conditions 220*b* (which may be detected by the external camera 118*a*), traction 220*c*, external temperature 220*d*, internal temperature 220*e*, GPS location 220*f*, rain level 220*g*, and speed 220*h*.

As discussed above and as will be discussed in further detail below, the processor 318 of the problematic situation detection module 310 is adapted to analyze the environmental characteristics and any environmental characteristic measurements to determine whether the environmental conditions surrounding the vehicle 110, for example, are normal or abnormal. In some examples that are not intended to be limiting, the environmental conditions surrounding the vehicle 110 are normal if there is no rain, the vehicle 110 has good traction, and the vehicle 110 is not near a dangerous condition (e.g., a crash, an animal on the road, etc.). Each vehicle in the detection system 100 has a vehicle profile specific to that vehicle. For example, the vehicle 110 has a vehicle profile that may be different from the vehicle profile for the vehicle 120. In several embodiments, the vehicle profile 220 corresponds to the vehicle 110. As shown in FIG. 1, the vehicle 110 and the vehicle 120 are each in the same geographic area 180. Therefore, in some embodiments, the vehicle profiles for each of the vehicles 110, 120 may be similar. For example, the road conditions, external temperature, GPS location, and rain level may be substantially similar between the vehicle profiles for the vehicles 110 and 120. As will be discussed in further detail below, the processor 318 is adapted to compare vehicle profiles of one or more different vehicles in the same geographic area to determine if the environmental conditions of the target vehicle (e.g., the vehicle 110) are normal or abnormal.

Figure 5:
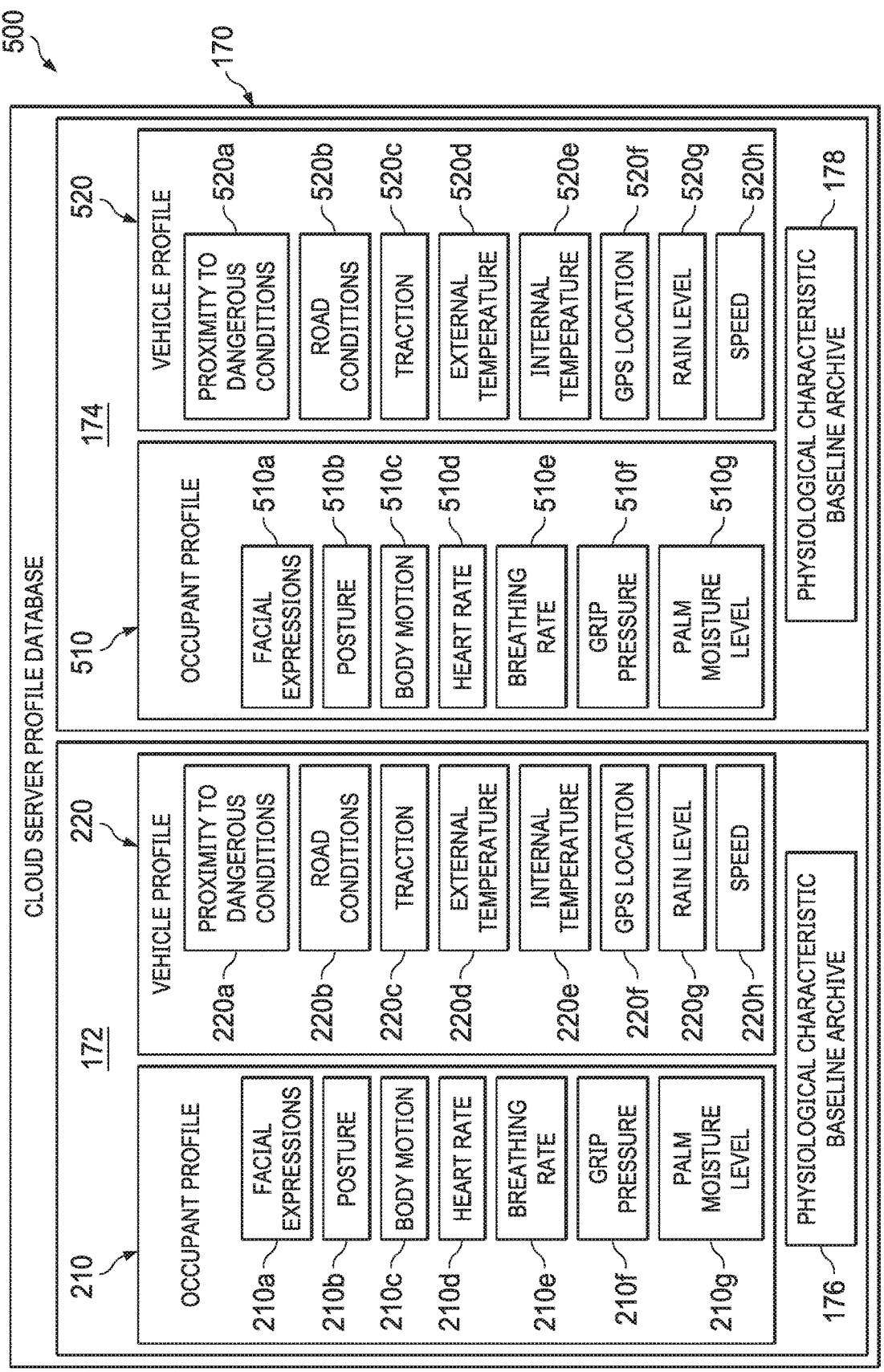
FIG. 5 is a diagrammatic illustration of a profile database according to one or more embodiments of the present disclosure.

FIG. 5 is a diagrammatic illustration of an apparatus according to one or more embodiments of the present disclosure. In at least one such embodiment, as illustrated in FIG. 5, the apparatus is generally referred to by the reference numeral 500 and includes the components of the apparatus 200 and the system 300, which components are given the same reference numerals. In the embodiment shown in FIG. 5, in addition to the apparatus 500 having certain components of the apparatus 200 and the system 300, the profile database 170 of the apparatus 500 includes a directory 172 and a directory 174. As shown in FIG. 5, the directory 172 corresponds to the vehicle 110 and includes the occupant profile 210 and the vehicle profile 220. In several embodiments, the directory 172 also includes a physiological characteristic baseline archive 176. The baseline archive 176 is adapted to include the baselines determined for each physiological characteristic in the occupant profile 210, as discussed above and as will be discussed in further detail below. The baseline archive 176 is adapted to receive determined baselines corresponding to the vehicle 110 from the transmitter 314, as discussed above.

As further shown in FIG. 5, the directory 174 corresponds to the vehicle 120 and includes an occupant profile 510 and a vehicle profile 520. The occupant profile 510 is substantially similar to the occupant profile 210 and includes physiological characteristics of an occupant in the vehicle 120. In the embodiment shown in FIG. 5, the physiological characteristics in the occupant profile 510 include one or more facial expressions 510*a*, a posture 510*b*, body motion 510*c*, a heart rate 510*d*, a breathing rate 510*e*, a grip pressure 510*f*, and a palm moisture level 510*g*. The vehicle profile 520 is substantially similar to the vehicle profile 220 and includes environmental characteristics of the vehicle 120. In the embodiment shown in FIG. 5, the environmental characteristics in the vehicle profile 520 include a proximity to dangerous conditions 520*a* (which may be detected by an external camera 128*a*), road conditions 520*b* (which may be detected by the external camera 128*a*), traction 520*c*, external temperature 520*d*, internal temperature 520*e*, GPS location 520*f*, rain level 520*g*, and speed 520*h*. In several embodiments, the directory 174 also includes a physiological characteristic baseline archive 178. The baseline archive 178 is adapted to include the baselines determined for each physiological characteristic in the occupant profile 510, as discussed above and as will be discussed in further detail below. The baseline archive 178 is adapted to receive determined baselines corresponding to the vehicle 120 from the transmitter 314, as discussed above.

While not shown in FIG. 5, it is to be understood that the profile database 170 may also include a directory corresponding to each vehicle in the system 100 (e.g., the vehicles 130, 140, 150), and including components corresponding to those discussed above.

Figure 6:
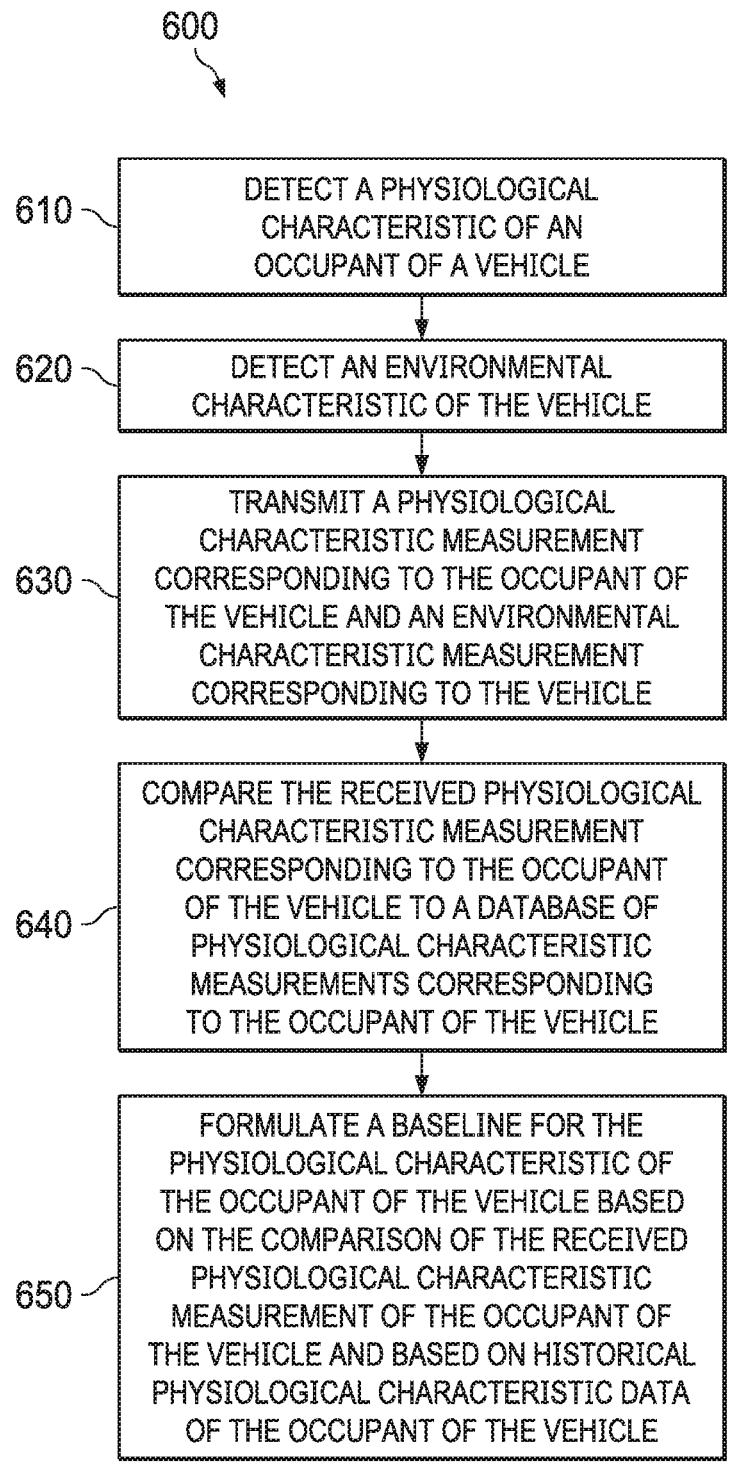
FIG. 6 is a flow chart illustration of a method of operating the system of FIGS. 1-5 according to one or more embodiments of the present disclosure.

FIG. 6 is a flow chart illustration of a method of operating the system of FIGS. 1-5 according to one or more embodiments of the present disclosure. In several embodiments, as discussed above, one or more sensors of the vehicle 110 are used to determine whether one or more of the occupants in the vehicle 110 is experiencing a medical emergency. One or more sensors 116 of the vehicle 110 are used to detect and/or record one or more physiological characteristics of an occupant of the vehicle 110. Additionally, one or more environmental sensors 118 are used to detect and/or record one or more environmental characteristics of the vehicle 110. The vehicle 110 transmits physiological characteristic measurements and environmental characteristic measurements to a server. The server receives the information, analyzes the information, and determines a proper response. It is an object of the server to confirm the accuracy of the received information before determining whether the vehicle occupant is actually experiencing a medical emergency. This helps reduce the number of false reports, which helps reduce the number of incorrectly-initiated responses. To achieve this end, the server compares a received physiological characteristic measurement corresponding to a specific vehicle occupant with a database of stored physiological characteristic measurements corresponding to the specific vehicle occupant. Continual comparisons allow the server to formulate a baseline for the physiological characteristic. The server then determines if a newly received physiological characteristic measurement is outside of the baseline. If the physiological characteristic measurement is outside of the baseline, the server compares the newly received physiological characteristic measurement with a physiological characteristic measurement corresponding to an occupant of one or more other vehicles (e.g., the vehicle 120). The server then analyzes the detected environmental characteristic data to determine if the environmental conditions of the vehicle 110 are normal or abnormal. If the environmental conditions of the vehicle 110 are normal, then the server determines that the vehicle occupant is experiencing a medical emergency, and the vehicle 110 initiates an appropriate response, as directed by the server.

In one such embodiment, as illustrated in FIG. 6, the method is generally referred to by the reference numeral 600 and includes at a step 610 detecting a physiological characteristic of an occupant of a vehicle. In some embodiments, the physiological characteristic is detected using the sensor 116 (see FIG. 2). In several examples, the sensor 116 transmits a detected physiological characteristic measurement corresponding to the occupant of the vehicle 110 to the profile generation module 114 of the vehicle 110. The physiological characteristic measurement may be received by the receiver 113 of the profile generation module 114. The receiver 113 may then output the physiological characteristic measurement to the sensor processing module 115 for further analysis and processing. In several embodiments, the physiological characteristic measurement may correspond to any one of the physiological characteristics discussed above with respect to FIG. 4A (e.g., one or more facial expressions 210*a*, the posture 210*b*, the body motion 210*c*, the heart rate 210*d*, the breathing rate 210*e*, the grip pressure 210*f*, and the palm moisture level 210*g*).

In some examples, as discussed above, the sensor 116 is adapted to capture images of objects, such as one or more occupants, within the interior of the vehicle 110. In such examples, the camera 116*a* is adapted to capture images and/or video of the occupant of the vehicle 110 (e.g., the driver of the vehicle 110). As discussed above, in some embodiments, the camera 116*a* transmits the captured images and/or video (which may be a physiological characteristic measurement) to the sensor processing module 115 of the profile generation module 114. In several examples, the sensor processing module 115 is adapted to analyze the captured images and/or video to track the facial expressions and/or posture of the vehicle occupant. In some embodiments, after the sensor processing module 115 processes each received image and/or video file, the profile generation module 114 transmits each processed file to the problematic situation detection module 310. In some examples, the processed files may be stored in the memory 316 of the problematic situation detection module 310. Therefore, in several embodiments, the memory 316 maintains a historical record of all image and/or video transmissions received from the profile generation module 114. In several other embodiments, the processed files may be stored in the profile database 170.

In an example that is not intended to be limiting, it may be important to track the facial expressions 210*a* of the vehicle occupant because certain facial expressions, such as pain, anger, or surprise, may indicate that the vehicle occupant is experiencing an emergency medical situation. As another non-limiting example, it may be important to track the posture 210*b* of the vehicle occupant because certain postures, such as slouching, hunching over, or leaning forward, may indicate that the vehicle occupant is experiencing an emergency medical situation. Similarly, as a further non-limiting example, it may be important to track the body motion 210*c* of the vehicle occupant because certain body motions, such as sudden, jerky movements, may indicate that the vehicle occupant is experiencing an emergency medical situation. In some examples, an indication that the vehicle occupant is experiencing an emergency medical situation may include one or more of an increase in heart rate 210*d*, breathing rate 210*e*, grip pressure 210*f*, and palm moisture level 210*g*. In several examples, to determine whether the vehicle occupant is experiencing a medical emergency situation, the data captured by the sensor 116 is augmented by data captured by the environmental sensor 118 (see FIG. 1), which will be discussed in further detail below.

At a step 620 before, during, or after detecting the physiological characteristic of an occupant of the vehicle 110, an environmental characteristic of the vehicle 110 is detected. In some embodiments, the environmental characteristic is detected using the environmental sensor 118 (see FIG. 2). In several examples, the environmental sensor 118 transmits a detected environmental characteristic measurement corresponding to the vehicle 110 to the profile generation module 114 of the vehicle 110. In several examples, the environmental characteristic measurement is received by the receiver 113 of the profile generation module 114. The receiver 113 may then output the environmental characteristic measurement to the sensor processing module 115 for further analysis and processing. In several embodiments, the environmental characteristic measurement may correspond to any one of the environmental characteristics discussed above with respect to FIG. 4B (e.g., the proximity to dangerous conditions 220a, the road conditions 220b, the traction 220c, the external temperature 220d, the internal temperature 220e, the GPS location 220f, the rain level 220g, and the speed 220h).

In some examples, as discussed above, the environmental sensor 118 is adapted to capture images and/or video of objects, such as other vehicles and/or the road surface, within a proximity surrounding the vehicle 110. In such examples, the external camera 118a is adapted to capture images and/or video (which may be an environmental characteristic measurement) of the objects and/or road surface surrounding the vehicle 110. As discussed above, in some embodiments, the external camera 118a transmits the captured images and/or video to the sensor processing module 115 of the profile generation module 114. In several examples, the sensor processing module 115 is adapted to analyze the captured images and/or video to track the environmental conditions surrounding the vehicle 110. In some embodiments, after the sensor processing module 115 processes each received image and/or video file, the profile generation module 114 transmits each processed file to the problematic situation detection module 310. In several embodiments, the processed files may be stored in the memory 316 of the problematic situation detection module 310. Therefore, in several embodiments, the memory 316 maintains a historical record of all image and/or video transmissions received from the profile generation module 114. In several other embodiments, the processed files may be stored in the profile database 170.

In an example that is not intended to be limiting, it may be important to determine the vehicle 110's proximity to dangerous conditions 220a because certain environmental conditions, such as a crash, an erratic driver, or a lightning strike, may indicate that the environmental characteristics surrounding the vehicle are abnormal. As another non-limiting example, it may be important to track the GPS location 220f of the vehicle 110 in order to determine the weather conditions at the location of the vehicle 110. Certain weather conditions, such as a tornado, a lightning strike, or a thunderstorm, may indicate that the environmental conditions surrounding the vehicle 110 are abnormal. Similarly, as a further non-limiting example, it may be important to track the speed 220h of the vehicle 110 because high vehicle speeds may indicate that the environmental conditions surrounding the vehicle 110 are abnormal. In some examples, an indication that the environmental conditions surrounding the vehicle 110 are abnormal may include one or more of close proximity to dangerous conditions 220a, poor road conditions 220b, poor traction 220c, low external temperature 220d, normal internal temperature 220e, high rain level 220g, and high speed 220h. In several examples, to determine whether the environmental conditions surrounding the vehicle 110, the data captured by the environmental sensor 118 is augmented by the data captured by the sensor 116, which will be discussed in further detail below.

At a step 630 during or after detecting the physiological characteristic of an occupant of the vehicle 110 and/or the environmental characteristic of the vehicle 110, the physiological characteristic measurement corresponding to the occupant of the vehicle 110 and the environmental characteristic measurement corresponding to the vehicle 110 are transmitted by the profile generation module 114. In several embodiments, the transmitter 117 of the profile generation module 114 transmits the physiological characteristic measurement and the environmental characteristic measurement to the problematic situation detection module 310 of the server 160. In some examples, as discussed above, the physiological characteristic measurement and the environmental characteristic measurement may be stored in the memory 316. In other examples, the transmitter 117 transmits the physiological characteristic measurement and the environmental characteristic measurement to the profile database 170. In further examples, the transmitter 117 transmits the physiological characteristic measurement and the environmental characteristic measurement to both the memory 316 and the profile database 170.

When transmitted, the physiological characteristic measurement and the environmental characteristic measurement are each associated with an identifier (e.g., a data tag, a file identifier, etc.). The identifier for each physiological characteristic measurement maps each detected physiological characteristic measurement to a specific vehicle occupant (e.g., the driver of the vehicle 110). The identifier for each environmental characteristic measurement maps each detected environmental characteristic measurement to a specific vehicle (e.g., the vehicle 110). In several embodiments, the identifiers allow each physiological characteristic measurement to be associated with the proper vehicle occupant, and the identifiers allow each environmental characteristic measurement to be associated with the proper vehicle. In such embodiments, this facilitates the formulation of a baseline for each physiological characteristic for a specific vehicle occupant, which will be discussed in further detail below. Further, in such embodiments, the identifiers aid in the determination of the environmental conditions for a specific vehicle, which will be discussed in further detail below.

In several embodiments, the physiological characteristic measurement and the environmental characteristic measurement are received by the server 160. In such embodiments, the physiological and environmental characteristic measurements are received by the receiver 312 of the problematic situation detection module 310. In several alternative embodiments, the physiological and environmental characteristic measurements are received by the profile database 170 either directly from the profile generation module 114 of the vehicle 110 or indirectly via the problematic situation detection module 310 of the server 160, as discussed above. When received, the physiological characteristic measurement and the environmental characteristic measurement are separated and categorized based on the respective identifier for each characteristic. For example, a heart rate measurement corresponding to the driver of the vehicle 110 may be transmitted to the directory 172.

At a step 640 during or after transmitting the physiological and environmental characteristic measurements, the physiological characteristic measurement corresponding to the occupant of the vehicle is compared to a database of physiological characteristic measurements corresponding to the occupant of the vehicle. In several embodiments, the database may be the profile database 170. In several examples, the profile database 170 includes historical physiological characteristic data of an occupant of a vehicle (e.g., the driver of the vehicle 110). In some embodiments, the processor 318 of the problematic situation detection module 310 of the server 160 compares the received physiological characteristic measurement to the database of historical physiological characteristics. For exemplary and clarity purposes only, the following discussion will be made with respect to a heart rate (e.g., the heart rate 210d) of a driver of a vehicle (e.g., the driver of the vehicle 110). The heart rate 210d is only meant to be an example of one physiological characteristic. The following discussion applies to any other physiological characteristic for any other vehicle occupant as well.

In several embodiments, a received heart rate measurement 210d (which may be a physiological characteristic measurement) for the driver of the vehicle 110 is compared with previously received heart rate measurements 210d (i.e., historical heart rate measurements) that may be stored in the profile database 170. In such embodiments, the previously received heart rate measurements 210d may be stored in the directory 172 corresponding to the vehicle 110. The previously received heart rate measurements 210d may further be stored in the occupant profile 210 in the directory 172. In several alternative embodiments, the previously received heart rate measurements 210d may be transmitted to the profile generation module 114 and stored in the occupant profile 210 in the profile generation module 114. As discussed above, each received heart rate measurement 210d may be stored for a set period of time, which may be less than one minute or more than ten minutes, for example. In several embodiments, the processor 318 compares each new received heart rate measurement 210d with the database of heart rate measurements, which may be included in the directory 172, for example.

At a step 650 during or after comparing the physiological characteristic measurement to the database of physiological characteristic measurements, a baseline for the physiological characteristic is formulated. In several embodiments, the processor 318 formulates the baseline for the physiological characteristic, which may be the heart rate 210d of the driver of the vehicle 110. In some examples, the processor 318 is adapted to implement one or more machine learning algorithms to determine the baseline for the physiological characteristic by continually comparing received physiological characteristic data (e.g., physiological characteristic measurements) with historical physiological characteristic data (e.g., historical physiological characteristic measurements), which may be stored in the memory 316. In some embodiments, after the processor 318 determines the baseline for the physiological characteristic (e.g., the heart rate 210d), the processor 318 may transmit the baseline to the directory 172 where the baseline may be stored in the baseline archive 176 (see FIG. 5). In several embodiments, the baseline for each physiological characteristic corresponding to vehicle 110 is stored in the baseline archive 176. Therefore, in some examples, the problematic situation detection module 310 compares each new received physiological characteristic measurement with the baseline stored in the baseline archive 176.

In several embodiments, the problematic situation detection module 310 then confirms the accuracy of the received information to determine whether the vehicle occupant is actually experiencing a medical emergency situation. For example, the processor 318 determines whether the received physiological characteristic measurement of the vehicle occupant is outside of the baseline. In some examples, after determining that the received physiological characteristic measurement is outside of the baseline, the processor 318 determines whether the received physiological characteristic measurement is similar to a physiological characteristic measurement corresponding to one or more other vehicles (e.g., the vehicle 120). In some embodiments, the processor 318 may compare the received physiological characteristic measurement with a physiological characteristic measurement corresponding to an occupant of one other vehicle, two other vehicles, three other vehicles, four other vehicles, five other vehicles, ten other vehicles, or any other suitable number of other vehicles. In several embodiments, the processor 318 then determines whether the environmental conditions of the vehicle 110 are normal. After a determination that the environmental characteristic is normal, then the processor 318 determines that the vehicle occupant (e.g., the driver of the vehicle 110) is experiencing an emergency situation.

In several examples, the response determination module 320 then determines an emergency response. In several embodiments, the response determination module 320 transmits the determined emergency response to the profile generation module 114 of the vehicle 110. Then, in such embodiments, the profile generation module 114 initiates the emergency response. For example, if the driver of the vehicle 110 is experiencing a heart attack, the response determination module 320 may instruct the profile generation module 114 to command the vehicle 110 to automatically stop moving, activate hazard signals, and transmit a GPS signal to the server 160. In several embodiments, the server 160 is connected to and transmits the heart attack information to hospitals, ambulances, fire trucks, and other similar emergency responders. In further examples, when an emergency situation is detected while the vehicle 110 is operating in a non-autonomous driving mode, the response determination module 320 may automatically initiate an autonomous driving mode of the vehicle 110, if available. In several additional examples, the vehicle 110 may communicate with other vehicles in the same geographic area (e.g., the geographic area 180) as the vehicle 110 through vehicle-to-vehicle (V2V) communication. In such examples, the vehicle 110 may use V2V communication to generate the best and/or fastest route to a hospital or other appropriate medical care facility.

Figure 7:
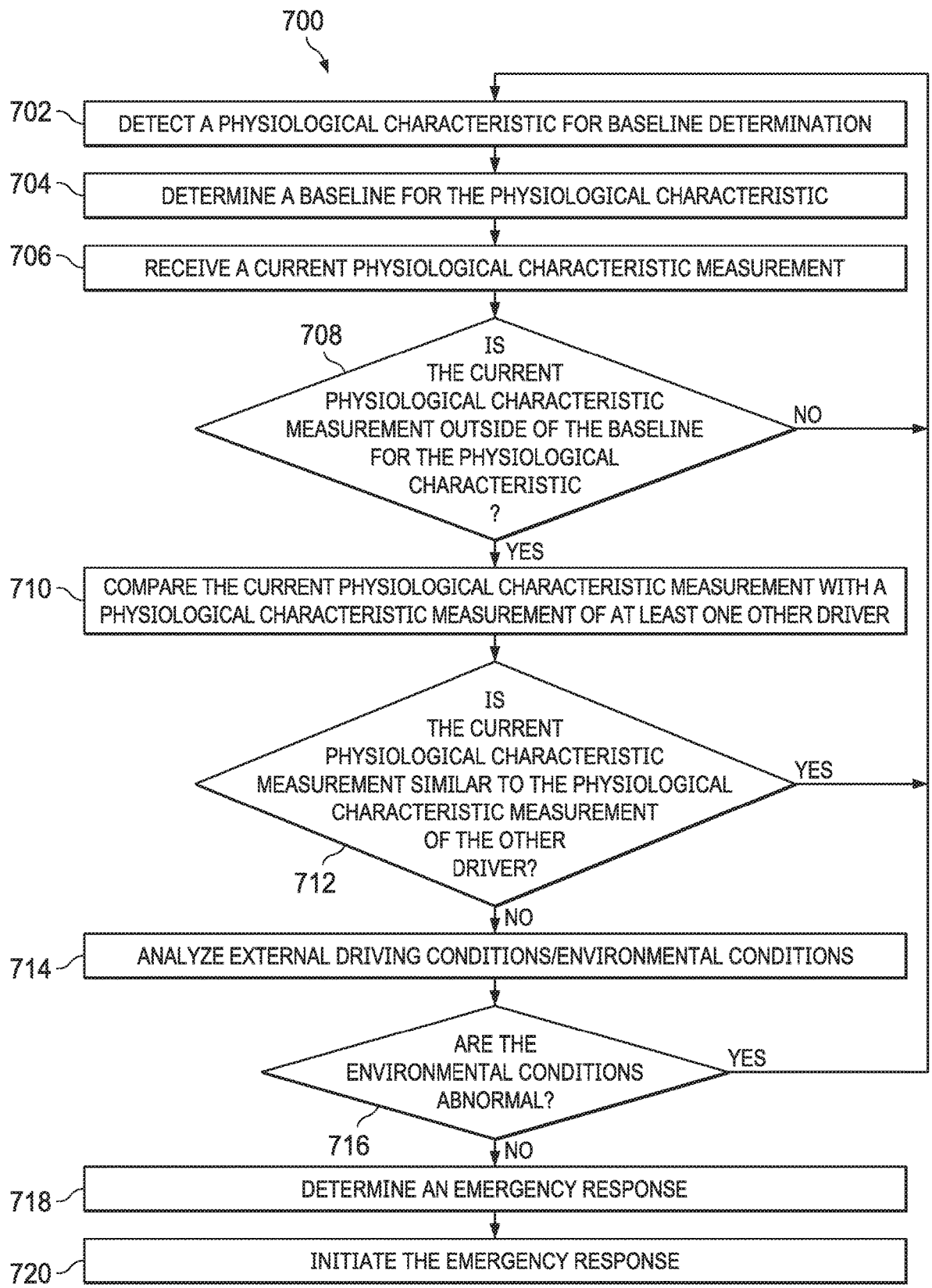
FIG. 7 is a flow diagram illustration of a method of operating the system of FIGS. 1-5 according to one or more embodiments of the present disclosure.

FIG. 7 is a flow diagram illustration of a method of operating the system of FIGS. 1-5 according to one or more embodiments of the present disclosure. In one such embodiment, as illustrated in FIG. 7, the method is generally referred to by the reference numeral 700 and is illustrated as a set of operations or steps 702 through 720 and is described with continuing reference to FIGS. 1-5. Not all of the illustrated steps 702 through 720 may be performed in all embodiments of the method 700. Additionally, one or more steps that are not expressly illustrated in FIG. 7 may be included before, after, in between, or as part of the steps 702 through 720. In some embodiments, one or more of the steps 702 through 720 may be implemented, at least in part, in the form of executable code stored on non-transitory, tangible, machine-readable media that when run by one or more processors may cause the one or more processors to perform one or more of the processes. In one or more embodiments, the steps 702 through 720 may be performed by the detection system 100 from FIG. 1.

In one such embodiment, as illustrated in FIG. 7, the method is generally referred to by the reference numeral 700 and includes at a step 702 detecting a physiological characteristic of an occupant of a vehicle (e.g., the vehicle 110) to be used to create a baseline. As discussed above with respect to FIG. 6, in some embodiments, the physiological characteristic is detected using the sensor 116 (see FIG. 2). In several examples, the sensor 116 transmits a detected physiological characteristic measurement corresponding to the occupant of the vehicle 110 to the profile generation module 114 of the vehicle 110. The physiological characteristic measurement may be received by the receiver 113 of the profile generation module 114. The receiver 113 may then output the physiological characteristic measurement to the sensor processing module 115 for further analysis and processing. In several embodiments, the physiological characteristic measurement may correspond to any one of the physiological characteristics discussed above with respect to FIG. 4A (e.g., one or more facial expressions 210a, the posture 210b, the body motion 210c, the heart rate 210d, the breathing rate 210e, the grip pressure 210f, and the palm moisture level 210g).

In several embodiments, at a step 704 during or after detecting the physiological characteristic of the vehicle, a baseline for the physiological characteristic is determined. As discussed above with respect to FIG. 6, in several embodiments, the processor 318 determines the baseline for the physiological characteristic, which may be the heart rate 210d of the driver of the vehicle 110. In some examples, the processor 318 is adapted to implement one or more machine learning algorithms to determine the baseline for the physiological characteristic by continually comparing received physiological characteristic data (e.g., physiological characteristic measurements) with historical physiological characteristic data (e.g., historical physiological characteristic measurements), which may be stored in the memory 316. In some embodiments, after the processor 318 determines the baseline for the physiological characteristic (e.g., the heart rate 210d), the processor 318 may transmit the baseline to the directory 172 where the baseline may be stored in the baseline archive 176 (see FIG. 5). In several embodiments, the baseline for each physiological characteristic corresponding to vehicle 110 is stored in the baseline archive 176. Therefore, in some examples, the problematic situation detection module 310 compares each new received physiological characteristic measurement with the baseline stored in the baseline archive 176.

In several examples, at a step 706 during or after determining the baseline for the physiological characteristic, a current physiological characteristic measurement is received. In several embodiments, the current physiological characteristic is detected by one or more of the sensors 116, as discussed above. For example, as discussed above, the heart rate sensor 116b is adapted to detect, monitor, and/or record heart rate measurements 210d of the driver of the vehicle 110.

In some embodiments, at a step 708 during or after receiving the current physiological characteristic measurement, the detection system 100 determines whether the current physiological characteristic measurement is outside the baseline for that particular physiological characteristic. In several examples, the processor 318 of the problematic situation detection module 310 compares the current physiological characteristic measurement with the determined baseline for that particular physiological characteristic. In one example that is not intended to be limiting, the detection system 100 may determine that the baseline for the heart rate 210d of the driver of the vehicle 110 is a range between 60 beats per minute (BPM) and 65 BPM. The processor 318, for example, then compares a currently detected heart rate measurement 210d (which may be a current physiological characteristic measurement) with the determined baseline, which may be stored in the baseline archive 176, for example. If the current heart rate measurement 210d is either below 60 BPM or above 65 BPM, as recorded by the heart rate sensor 116b (which may be located in a seatbelt of the vehicle 110, for example), then the processor 318 determines that the current heart rate measurement 210d is outside of the heart rate baseline, and the method 700 proceeds to step 710. If the current heart rate measurement 210d is 60 BPM, 65 BPM, or any BPM measurement between 60 BPM and 65 BPM, as recorded by the heart rate sensor 116b, then the processor 318 determines that the current heart rate measurement 210d is within the heart rate baseline, and the method 700 returns to step 702.

In several embodiments, at a step 710 during or after determining that the current physiological characteristic measurement is outside of the baseline for that physiological characteristic, the detection system 100 compares the current physiological characteristic measurement with a physiological characteristic measurement of at least one occupant of another vehicle (e.g., the vehicle 120). In some examples, as discussed above, the processor 318 compares physiological characteristic measurements of one or more vehicle occupants in one or more vehicles within the same geographic area (e.g., the geographic area 180) to reduce the occurrence of false-positive results. In such examples, the processor 318 may compare the physiological characteristic measurements of one or more vehicle occupants in two vehicles, three vehicles, four vehicles, five vehicles, ten vehicles, or any other suitable number of vehicles within the same geographic area. In such examples, physiological characteristic data for the vehicle 120, for example, may be stored in the directory 174 of the profile database 170. In alternative examples, the physiological characteristic data for the vehicle 120, for example, may be stored in the memory 316 of the problematic situation detection module 310 of the server 160.

In several examples, at a step 712 during or after comparing the current physiological characteristic measurement of the driver of the vehicle 110 with the physiological characteristics of at least one occupant of another vehicle (e.g., the vehicle 120), the detection system 100 determines whether the compared physiological characteristic measurements are similar. In some embodiments, this determination is made by the processor 318 of the problematic situation detection module 310.

In an example that is not intended the be limiting, the processor 318 may compare the current heart rate measurement 210d of the driver of the vehicle 110 with a current heart rate measurement of a driver of the vehicle 120. The processor 318 may also compare the current heart rate measurement 210d of the driver of the vehicle 110 with a current heart rate measurement of a driver of any other one or more vehicles that may be located within the geographic area 180. The current heart rate measurement 210d of the driver of the vehicle 110 may be recorded as 120 BPM, which is well outside of the 60 BPM-65 BPM baseline for the heart rate measurement, as discussed above. This increase in heart rate may be an indication that the driver is experiencing a cardiac emergency, or it may be an indication that the driver was suddenly startled, for example. Therefore, the detection system 100 compares the heart rate measurement 210d of the driver of the vehicle 110 with the heart rate measurement of other drivers in the same geographic area to determine if the driver of the vehicle 110 is actually experiencing a medical emergency. In several embodiments, if the heart rate 210d of driver of the vehicle 110 is elevated, and the heart rates of other drivers in the geographic area 180 are not elevated, this may be an indication that the driver of the vehicle 110 is experiencing a medical emergency, such as a heart attack. On the other hand, in several examples, if the heart rate 210d of driver of the vehicle 110 is elevated, and the heart rates of other drivers in the geographic area 180 are also elevated, this may be an indication that the driver of the vehicle 110 is not experiencing a medical emergency. In such examples, this may be an indication that the drivers with elevated heart rates witnessed a startling event (e.g., a car crash, a sudden nearby lightning strike, etc.). If the heart rate measurement 210d of the driver of the vehicle 110 is much higher than the heart rate measurement of the driver of the vehicle 120, for example, (e.g., 120 BPM as compared to 64 BPM), then the processor 318 determines that the heart rate measurements are not similar, and the method 700 proceeds to step 714. If the heart rate measurement 210d of the driver of the vehicle 110 is close to the heart rate measurement of the driver of the vehicle 120, for example, (e.g., 120 BPM as compared to 115 BPM), then the processor 318 determines that the heart rate measurements are similar, and the method 700 returns to step 702.

In several examples, at a step 714 during or after determining that the physiological characteristic measurement of the vehicle occupant is not similar to the physiological characteristic measurement of an occupant of another vehicle, the environmental conditions of the vehicle (e.g., the vehicle 110) are analyzed. In some examples, the environmental conditions may be the driving conditions experienced by a vehicle (e.g., the vehicle 110). In some embodiments, even when the current physiological characteristic measurement is outside of the baseline, a further validation step may occur to ensure that any final determinations made by the detection system 100 are accurate. In such embodiments, as discussed above with respect to FIG. 6, an environmental characteristic measurement of the vehicle 110 is detected and analyzed. In some embodiments, the environmental characteristic is detected using the environmental sensor 118 (see FIG. 2). In several examples, the environmental sensor 118 transmits a detected environmental characteristic measurement corresponding to the vehicle 110 to the profile generation module 114 of the vehicle 110. In several examples, the environmental characteristic measurement is received by the receiver 113 of the profile generation module 114. The receiver 113 may then output the environmental characteristic measurement to the sensor processing module 115 for further analysis and processing. In several embodiments, the environmental characteristic measurement may correspond to any one of the environmental characteristics discussed above with respect to FIG. 4B (e.g., the proximity to dangerous conditions 220a, the road conditions 220b, the traction 220c, the external temperature 220d, the internal temperature 220e, the GPS location 220f, the rain level 220g, and the speed 220h).

In several examples, at a step 716, during or after analyzing the environmental conditions of the vehicle 110, the detection system 100 determines whether the environmental conditions are normal or abnormal. In some examples, this determination may be made by the processor 318 of the problematic situation detection module 310.

When, for example, the heart rate 210d of the driver of the vehicle 110 is elevated and the heart rates of occupants of other vehicles in the geographic area 180 are not elevated, this may be an indication that the vehicle 110 experienced an abnormal environmental condition that the other vehicles (e.g., the vehicle 120) did not experience. As a non-limiting example, the vehicle 110 may suddenly lose traction, as detected by the traction sensor 118b, for example, whereas the vehicle 120 may not have lost traction. In such an example, this loss of traction for the vehicle 110 may cause an increase in heart rate of the driver of the vehicle 110, but the heart rate of the driver of the vehicle 120 may not have increased because the vehicle 120 did not experience an abnormal environmental condition (e.g., loss of traction). In embodiments where the heart rate 210d of the driver of the vehicle 110 is not similar to the heart rate of the driver of the vehicle 120 but the environmental conditions of the vehicle 110 are abnormal, the detection system 100 may determine that the driver of the vehicle 110 is not experiencing a medical emergency. As such, if the traction sensor 118b does not detect a sudden loss of traction, for example, and there are no other abnormal environmental conditions, then the processor 318 may determine that the environmental conditions of the vehicle 110 are not abnormal (i.e., the environmental conditions are normal), and the method 700 proceeds to step 716. On the other hand, if the traction sensor 118b detects a sudden loss of traction, for example, then the processor 318 may determine that the environmental conditions of the vehicle 110 are abnormal, and the method 700 returns to step 702.

In several embodiments, at a step 718 during or after determining that the environmental conditions of the vehicle 110 are normal, an emergency response is determined. In several examples, as discussed above with respect to FIG. 6, the processor 324 of the response determination module 320 determines an emergency response. The emergency response may be tailored according to the detected physiological characteristic measurement corresponding to the occupant of the vehicle 110 and the detected environmental characteristic measurement corresponding to the vehicle 110. As a non-limiting example, if the driver of the vehicle 110 is experiencing a heart attack, the processor 324 may determine that the appropriate response is to contact a hospital, an ambulance, and an emergency contact of the driver of the vehicle 110. The processor 324 may also determine that the vehicle 110 should switch from a non-autonomous driving mode to an autonomous driving mode, if available, in order to automatically drive the vehicle 110 to the side of the road or to drive the vehicle 110 to a nearby hospital. In several embodiments, the response determination module 320 transmits the determined emergency response to the profile generation module 114 of the vehicle 110.

At a step 720, during or after determining the emergency response, the emergency response is initiated. As discussed above with respect to FIG. 6, the profile generation module 114 may initiate the emergency response. For example, if the driver of the vehicle 110 is experiencing a heart attack, the response determination module 320 may instruct the profile generation module 114 to command the vehicle 110 to automatically stop moving, activate hazard signals, and transmit a GPS signal to the server 160. In several embodiments, the server 160 is connected to and transmits the heart attack information to hospitals, ambulances, fire trucks, and other similar emergency responders. In further examples, when an emergency situation is detected while the vehicle 110 is operating in a non-autonomous driving mode, the response determination module 320 may automatically initiate an autonomous driving mode of the vehicle 110, if available. In several additional examples, the vehicle 110 may communicate with other vehicles in the same geographic area (e.g., the geographic area 180) as the vehicle

110 through vehicle-to-vehicle (V2V) communication. In such examples, the vehicle 110 may use V2V communication to generate the best and/or fastest route to a hospital or other appropriate medical care facility.

In several embodiments, a computer system typically includes at least hardware capable of executing machine readable instructions, as well as the software for executing acts (typically machine-readable instructions) that produce a desired result. In several embodiments, a computer system may include hybrids of hardware and software, as well as computer sub-systems.

In several embodiments, hardware generally includes at least processor-capable platforms, such as client-machines (also known as personal computers or servers), and hand-held processing devices (such as smart phones, tablet computers, personal digital assistants (PDAs), or personal computing devices (PCDs), for example). In several embodiments, hardware may include any physical device that is capable of storing machine-readable instructions, such as memory or other data storage devices. In several embodiments, other forms of hardware include hardware sub-systems, including transfer devices such as modems, modem cards, ports, and port cards, for example.

In several embodiments, software includes any machine code stored in any memory medium, such as RAM or ROM, and machine code stored on other devices (such as floppy disks, flash memory, or a CD ROM, for example). In several embodiments, software may include source or object code. In several embodiments, software encompasses any set of instructions capable of being executed on a node such as, for example, on a client machine or server.

In several embodiments, combinations of software and hardware could also be used for providing enhanced functionality and performance for certain embodiments of the present disclosure. In an embodiment, software functions may be directly manufactured into a silicon chip. Accordingly, it should be understood that combinations of hardware and software are also included within the definition of a computer system and are thus envisioned by the present disclosure as possible equivalent structures and equivalent methods.

In several embodiments, computer readable mediums include, for example, passive data storage, such as a random access memory (RAM) as well as semi-permanent data storage such as a compact disk read only memory (CD-ROM). One or more embodiments of the present disclosure may be embodied in the RAM of a computer to transform a standard computer into a new specific computing machine. In several embodiments, data structures are defined organizations of data that may enable an embodiment of the present disclosure. In an embodiment, a data structure may provide an organization of data, or an organization of executable code.

In several embodiments, any networks and/or one or more portions thereof, may be designed to work on any specific architecture. In an embodiment, one or more portions of any networks may be executed on a single computer, local area networks, client-server networks, wide area networks, internets, hand-held and other portable and wireless devices and networks.

In several embodiments, a database may be any standard or proprietary database software, such as Oracle, Microsoft Access, SyBase, or DBase II, for example. In several embodiments, the database may have fields, records, data, and other database elements that may be associated through database specific software. In several embodiments, data may be mapped. In several embodiments, mapping is the process of associating one data entry with another data entry. In an embodiment, the data contained in the location of a character file can be mapped to a field in a second table. In several embodiments, the physical location of the database is not limiting, and the database may be distributed. In an embodiment, the database may exist remotely from the server, and run on a separate platform. In an embodiment, the database may be accessible across the Internet. In several embodiments, more than one database may be implemented.

In several embodiments, a plurality of instructions stored on a computer readable medium may be executed by one or more processors to cause the one or more processors to carry out or implement in whole or in part the above-described operation of each of the above-described systems, methods, and/or any combination thereof. In several embodiments, such a processor may include one or more of any processor(s) that are part of the components of the above-described systems, and/or any combination thereof, and such a computer readable medium may be distributed among one or more components of the above-described systems. In several embodiments, such a processor may execute the plurality of instructions in connection with a virtual computer system. In several embodiments, such a plurality of instructions may communicate directly with the one or more processors, and/or may interact with one or more operating systems, middleware, firmware, other applications, and/or any combination thereof, to cause the one or more processors to execute the instructions.

It is understood that variations may be made in the foregoing without departing from the scope of the present disclosure.

In some embodiments, the elements and teachings of the various embodiments may be combined in whole or in part in some or all of the embodiments. In addition, one or more of the elements and teachings of the various embodiments may be omitted, at least in part, and/or combined, at least in part, with one or more of the other elements and teachings of the various embodiments.

Any spatial references, such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In some embodiments, while different steps, processes, and procedures are described as appearing as distinct acts, one or more of the steps, one or more of the processes, and/or one or more of the procedures may also be performed in different orders, simultaneously, and/or sequentially. In some embodiments, the steps, processes, and/or procedures may be merged into one or more steps, processes, and/or procedures.

In some embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although some embodiments have been described in detail above, the embodiments described are illustrative only and are not limiting, and those skilled in the art will readily appreciate that many other modifications, changes, and/or substitutions are possible in the embodiments without materially departing from the novel teachings and advantages of the present disclosure. Accordingly, all such modifications, changes, and/or substitutions are intended to be included within the scope of this disclosure as defined in the following claims. In the claims, any means-plus-function clauses are intended to cover the structures described herein as performing the recited function and not only structural equivalents, but also equivalent structures. Moreover, it is the express intention of the borrower not to invoke 35 U.S.C. § 112, paragraph 6 for any limitations of any of the claims herein, except for those in which the claim expressly uses the word "means" together with an associated function.

What is claimed is:

1. A system for detecting a problematic health situation, the system comprising:
    a server; and
    a first vehicle comprising:
        a sensor configured to measure a physiological characteristic of an occupant of the first vehicle;
        an environmental sensor configured to measure an environmental characteristic of the first vehicle; and
        a profile generation module including a memory, the profile generation module configured to:
            store a physiological characteristic measurement corresponding to the occupant of the first vehicle in the memory;
            store an environmental characteristic measurement corresponding to the first vehicle in the memory; and
            transmit the physiological characteristic measurement and the environmental characteristic measurement to the server,
    wherein the server is configured to:
        compare the transmitted physiological characteristic measurement corresponding to the occupant of the first vehicle to a database of physiological characteristic measurements corresponding to the occupant of the first vehicle, wherein the database includes historical physiological characteristic data of the occupant of the first vehicle;
        formulate a baseline for the physiological characteristic of the occupant of the first vehicle based on the comparison of the transmitted physiological characteristic measurement and the historical physiological characteristic data of the occupant of the first vehicle;
        compare the transmitted physiological characteristic measurement corresponding to the occupant of the first vehicle to a physiological characteristic measurement corresponding to an occupant of a second vehicle; and
        determine whether the transmitted physiological characteristic measurement corresponding to the occupant of the first vehicle is similar to the physiological characteristic measurement corresponding to the occupant of the second vehicle.

2. The system of claim 1, wherein the server is further configured to:
    determine whether the physiological characteristic measurement is outside the baseline.

3. The system of claim 1, further comprising:
    the second vehicle comprising:
        a sensor configured to measure a physiological characteristic of an occupant of the second vehicle;
        an environmental sensor configured to measure an environmental characteristic of the second vehicle; and
        a profile generation module including a memory, the profile generation module configured to:
            store the physiological characteristic measurement corresponding to the occupant of the second vehicle in the memory;
            store the environmental characteristic measurement corresponding to the second vehicle in the memory; and
            transmit the physiological characteristic measurement corresponding to the occupant of the second vehicle and the environmental characteristic measurement corresponding to the second vehicle to the server.

4. The system of claim 3, wherein the server is further configured to:
    compare the transmitted physiological characteristic measurement corresponding to the occupant of the second vehicle to a database of physiological characteristic measurements corresponding to the occupant of the second vehicle, wherein the database includes historical physiological characteristic data of the occupant of the second vehicle; and
    formulate a baseline for the physiological characteristic of the occupant of the second vehicle based on the comparison of the transmitted physiological characteristic measurement corresponding to the occupant of the second vehicle and the historical physiological characteristic data of the occupant of the second vehicle.

5. The system of claim 1, wherein the server is further configured to:
    receive the transmitted environmental characteristic measurement corresponding to the first vehicle; and
    determine, based on the received environmental characteristic measurement corresponding to the first vehicle, whether environmental conditions of the first vehicle are abnormal.

6. The system of claim 5, wherein the server is further configured to:
    determine, based on a determination that the environmental conditions of the first vehicle are normal, that the occupant of the first vehicle is experiencing a problematic health situation;
    determine a response; and
    transmit the response.

7. The system of claim 6, wherein:
    the profile generation module of the first vehicle is further configured to initiate the response; and
    the server is further configured to contact emergency services.

8. The system of claim 1, wherein the sensor comprises at least one of an in-vehicle camera, a heart rate sensor, a motion sensor, a pressure sensor, or a hydroscopic sensor.

9. The system of claim 8, wherein the first vehicle further comprises a seatbelt including the heart rate sensor, and wherein the heart rate sensor is configured to measure a heart rate of the occupant of the first vehicle.

10. A system for detecting a problematic health situation, the system comprising:
    a first vehicle comprising:
        a sensor configured to measure a physiological characteristic of an occupant of the first vehicle;
        an environmental sensor configured to measure an environmental characteristic of the first vehicle; and
        a profile generation module including a memory; and
    a server configured to:
        compare a physiological characteristic measurement corresponding to the occupant of the first vehicle to a database of physiological characteristic measurements corresponding to the occupant of the first vehicle, wherein the database includes historical physiological characteristic data of the occupant of the first vehicle;

formulate a baseline for the physiological characteristic of the occupant of the first vehicle based on the comparison of the physiological characteristic measurement corresponding to the occupant of the first vehicle and the historical physiological characteristic data of the occupant of the first vehicle;

determine whether the physiological characteristic measurement is outside the baseline;

based on a determination that the physiological characteristic measurement is outside the baseline, determine whether an environmental characteristic measurement is abnormal; and based on a determination that the environmental characteristic measurement is normal, determine that the occupant of the first vehicle is experiencing a problematic health situation.

11. The system of claim 10, wherein determining whether the physiological characteristic measurement is outside the baseline is based on a comparison between the physiological characteristic measurement and the baseline.

12. The system of claim 10, further comprising:
a second vehicle comprising:
   a sensor configured to measure a physiological characteristic of an occupant of the second vehicle;
   an environmental sensor configured to measure an environmental characteristic of the second vehicle; and
   a profile generation module including a memory.

13. The system of claim 12, wherein the server is further configured to:
compare a physiological characteristic measurement corresponding to the occupant of the second vehicle to a database of physiological characteristic measurements corresponding to the occupant of the second vehicle, wherein the database includes historical physiological characteristic data of the occupant of the second vehicle; and
formulate a baseline for the physiological characteristic of the occupant of the second vehicle based on the comparison of the physiological characteristic measurement corresponding to the occupant of the second vehicle and the historical physiological characteristic data of the occupant of the second vehicle.

14. The system of claim 13, wherein the server is further configured to:
compare the physiological characteristic measurement corresponding to the occupant of the first vehicle to the physiological characteristic measurement corresponding to the occupant of the second vehicle;
determine whether the physiological characteristic measurement corresponding to the occupant of the first vehicle is similar to the physiological characteristic measurement corresponding to the occupant of the second vehicle; and
based on a determination that the physiological characteristic measurement corresponding to the occupant of the first vehicle is different from the physiological characteristic measurement corresponding to the occupant of the second vehicle, determine whether the environmental characteristic measurement corresponding to the first vehicle is abnormal based on a comparison between the environmental characteristic measurement corresponding to the first vehicle and the environmental characteristic measurement corresponding to the second vehicle.

15. The system of claim 10, wherein determining that the occupant of the first vehicle is experiencing a problematic health situation comprises:
determining that the physiological characteristic measurement is outside the baseline;
determining that the physiological characteristic measurement corresponding to the occupant of the first vehicle is different from a physiological characteristic measurement of an occupant of a second vehicle; and
determining that the environmental characteristic measurement is normal.

16. A method for detecting a problematic health situation, the method comprising:
measuring a physiological characteristic of an occupant of a vehicle;
measuring an environmental characteristic of the vehicle;
transmitting to a server, by a profile generation module of the vehicle, a physiological characteristic measurement corresponding to the occupant of the vehicle and an environmental characteristic measurement corresponding to the vehicle;
comparing the transmitted physiological characteristic measurement to a database of physiological characteristic measurements of the occupant of the vehicle, wherein the database includes historical physiological characteristic data of the occupant of the vehicle;
formulating a baseline for the physiological characteristic of the occupant of the vehicle based on the comparison of the transmitted physiological characteristic measurement and the historical physiological characteristic data of the occupant of the vehicle; and
determining that the occupant of the vehicle is experiencing a problematic health situation based on a determination that the transmitted physiological characteristic measurement is outside the baseline and that the transmitted environmental characteristic measurement is normal.

17. The method of claim 16, further comprising:
determining whether the transmitted physiological characteristic measurement is outside the baseline.

18. The method of claim 16, further comprising:
determining a response;
transmitting the response; and
initiating, by the profile generation module of the vehicle, the response.

19. The method of claim 18, wherein initiating the response comprises contacting, by the server, emergency services.

20. The method of claim 18, wherein determining that the occupant of the vehicle is experiencing the problematic health situation is further based on a determination that the physiological characteristic measurement corresponding to the occupant of the vehicle is different from a physiological characteristic measurement of an occupant of a second vehicle.

* * * * *